United States Patent
Zajac et al.

(10) Patent No.: US 8,840,619 B2
(45) Date of Patent: Sep. 23, 2014

(54) DOVETAIL METHOD OF ALLOGRAFT TRANSPLANTATION

(75) Inventors: Eric S. Zajac, Naples, FL (US); Timothy R. Hoover, Bonita Springs, FL (US); Ricardo Albertorio, Naples, FL (US); William C. Carapezza, Land O Lakes, FL (US)

(73) Assignee: Arthrex, Inc., Naples, FL (US)

( * ) Notice: Subject to any disclaimer, the term of this patent is extended or adjusted under 35 U.S.C. 154(b) by 613 days.

(21) Appl. No.: 12/750,433

(22) Filed: Mar. 30, 2010

(65) Prior Publication Data

US 2010/0256645 A1 Oct. 7, 2010

Related U.S. Application Data

(60) Provisional application No. 61/202,773, filed on Apr. 2, 2009.

(51) Int. Cl.
  *A61B 17/17* (2006.01)
  *A61F 2/38* (2006.01)

(52) U.S. Cl.
  CPC ........... *A61B 17/1764* (2013.01); *A61F 2/3872* (2013.01)
  USPC ............................................ 606/96; 623/14.12

(58) Field of Classification Search
  USPC ........ 606/96, 86 R, 87, 88, 98, 99; 623/14.12
  See application file for complete search history.

(56) References Cited

U.S. PATENT DOCUMENTS

| 2,200,120 | A | * | 5/1940 | Nauth | 606/97 |
| 4,920,958 | A | * | 5/1990 | Walt et al. | 606/96 |
| 5,139,520 | A | * | 8/1992 | Rosenberg | 606/87 |
| 7,124,762 | B2 | * | 10/2006 | Carter et al. | 128/898 |
| 2006/0271059 | A1 | * | 11/2006 | Reay-Young et al. | 606/96 |

* cited by examiner

*Primary Examiner* — Matthew Lawson
*Assistant Examiner* — Zade Coley
(74) *Attorney, Agent, or Firm* — Dickstein Shapiro LLP

(57) ABSTRACT

A technique for forming a dovetail shaped groove in bone necessary in allograft transplantation such as the meniscus or the Achilles tendon. The technique uses a single drill guide that is designed to create a dovetail shape in bone. The drill guide is provided with a first opening for receiving one drill sleeve placed in a fixed location, and a second opening having an oblong shape for receiving a second drill sleeve having an offset cannulation. The combination of the two drill sleeves allows the surgeon to place two guide pins and ream over each guide pin resulting in a dovetail shape in the bone.

4 Claims, 9 Drawing Sheets

DOVETAIL METHOD OF ALLOGRAFT TRANSPLANTATION

CROSS-REFERENCE TO RELATED APPLICATIONS

This application claims the benefit of U.S. Provisional Application No. 61/202,773 filed on Apr. 2, 2009, the entire disclosure of which is incorporated by reference herein.

FIELD OF THE INVENTION

The present invention relates to the field of surgery reconstruction, particularly, a method for performing an allograft transplant using a dovetail technique.

BACKGROUND OF THE INVENTION

A known method for inserting a meniscal allograft is the dovetail meniscal allograft technique disclosed in U.S. Pat. No. 7,124,762, herein incorporated by reference. According to this technique, a bone block with a trapezoidal shape is delivered to a recipient dovetail slot in the tibia, the formation of which requires the use of drill bits, dilators, and rasps. This method requires several steps and multiple instruments to perform (i.e., multiple cutting guides and/or free hand instruments to create the dovetail shape of the groove in the tibia).

A dovetail meniscal technique that is quicker and uses fewer instruments is needed. Also needed is a single cutting guide to create an outline for the dovetail shape that requires little modification after reaming.

SUMMARY OF THE INVENTION

The present invention provides methods and instruments for forming a dovetail shaped groove in bone necessary in allograft transplantation such as the meniscus or the Achilles tendon. The technique uses fewer instruments and takes less time. The technique uses a single drill guide that is designed to create a dovetail shape in bone. The drill guide is provided with a first opening for receiving one drill sleeve placed in a fixed location, and a second opening having an oblong shape for receiving a second drill sleeve having an offset cannulation. The combination of the two drill sleeves allows the surgeon to place two guide pins and ream over each guide pin resulting in a dovetail shape in the bone.

In one embodiment, the drill guide includes a body with two holes extending through the body. The drill guide includes a first cannulated sleeve within the first hole, and a cannulated sleeve within the second hole. The cannulation of the first sleeve is situated with regard to the cannulation of the second sleeve so that a plane formed through the centers of the two holes through the drill guide is non-parallel with a plane formed through the centers of the cannulations of the first and second sleeves.

In another embodiment the drill guide includes a body having four sides. The body also has a first hole extending through the body and a second hole extending through the body. The drill guide also includes a first cannulated sleeve within the first hole, and a second cannulated sleeve within the second hole. The cannulation of the first sleeve is situated with regard to the cannulation of the second sleeve so that the centers of the two cannulations are offset in two dimensions and the center of the cannulation of the first sleeve is proximal to the first and second sides of the body and the center of the cannulation of the second sleeve is distal to the first and second sides of the body.

A method of surgery is also disclosed. In one embodiment, the method includes providing a body, the body having first and second holes that extend through the body. Additionally, a first cannulated sleeve is placed within the first hole, and a second cannulated sleeve is placed within the second hole. The cannulation of the first sleeve is situated with regard to the cannulation of the second sleeve so that a plane that intersects the centers of the two holes is non-parallel with a plane that intersects the centers of the cannulations of the two sleeves.

The method also includes placing a first guide pin within the cannulation of the first sleeve and placing a second guide pin within the cannulation of the second sleeve and inserting the first and second guide pins into a bone. Further, the first and second guide pins are used to guide a drill to create first and second channels in the bone so that an allograft implant may be placed within the first and second channels.

These and other features and advantages will be more apparent from the following detailed description that is provided in connection with the accompanying drawing and illustrated exemplary embodiments.

DETAILED DESCRIPTION OF THE PREFERRED EMBODIMENTS

Figure 1:
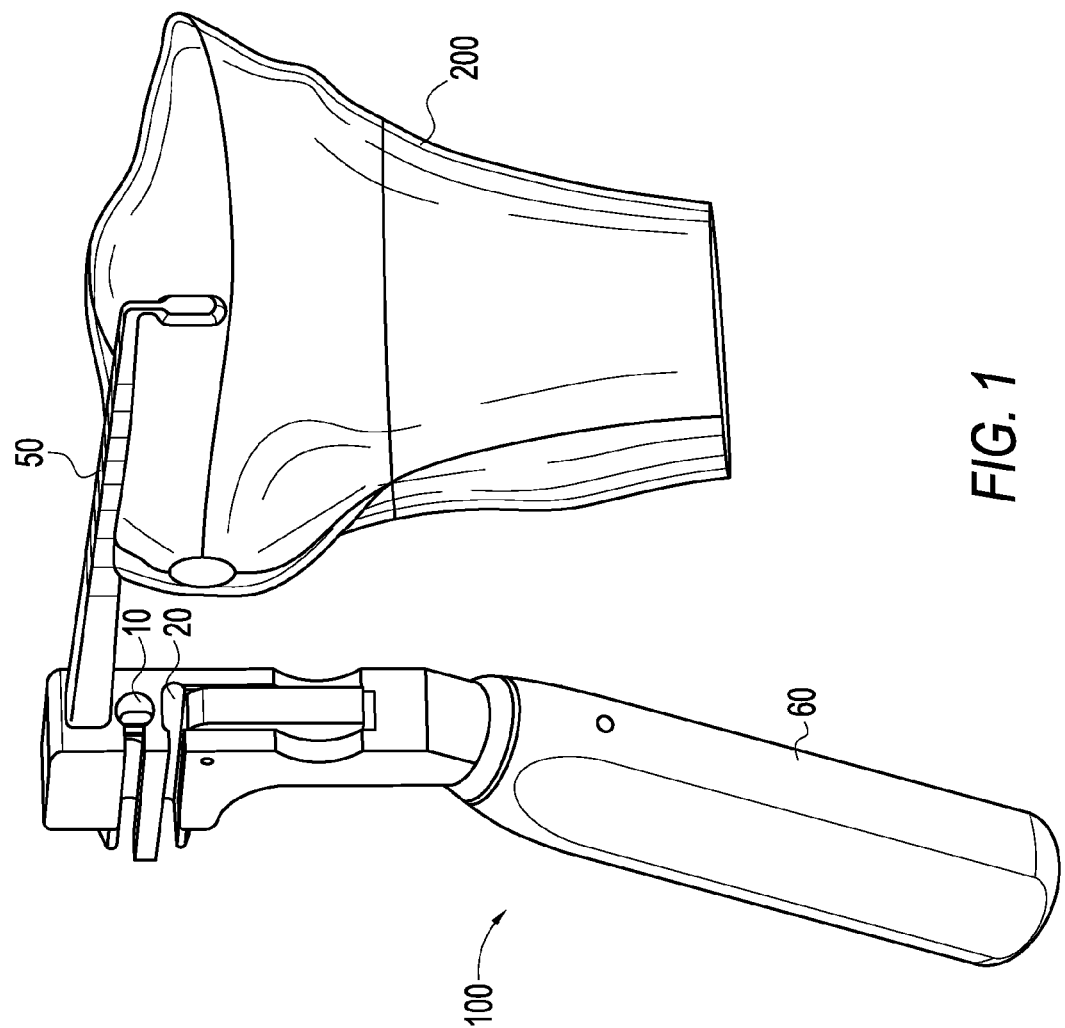
FIG. 1 illustrates a side view of a drill guide used for a meniscal allograft transplant procedure, with the marking hook positioning the drill guide with respect to the tibia.

The present invention provides a technique for forming a longitudinal groove in bone, the groove having a dovetail or trapezoidal cross-section for implantation of an allograft such as a meniscal or Achilles allograft.

The present invention also provides instruments for forming the dovetail shaped groove in bone necessary in allograft transplantation. A single drill guide is designed to create a dovetail shape in bone. The single drill guide is a double socket drill guide used to precisely place two guide pins that the surgeon can then ream over to create a dovetail shape in the tibia. The drill guide is provided with a first opening for receiving a first drill sleeve placed in a fixed location, and a second opening having an oblong shape for receiving a second drill sleeve having an offset cannulation. The first drill sleeve is round and placed at a constant location. The second drill sleeve has an oblong shape with an offset from the center cannulation, the oblong drill sleeve creating the left and right offset based on which way is inserted into the guide.

Referring now to the drawings, where like elements are designated by like reference numerals, FIGS. 1-9 illustrate an exemplary technique of forming a longitudinal dovetail groove that accommodates a dovetail meniscal allograft implant.

Figure 8:
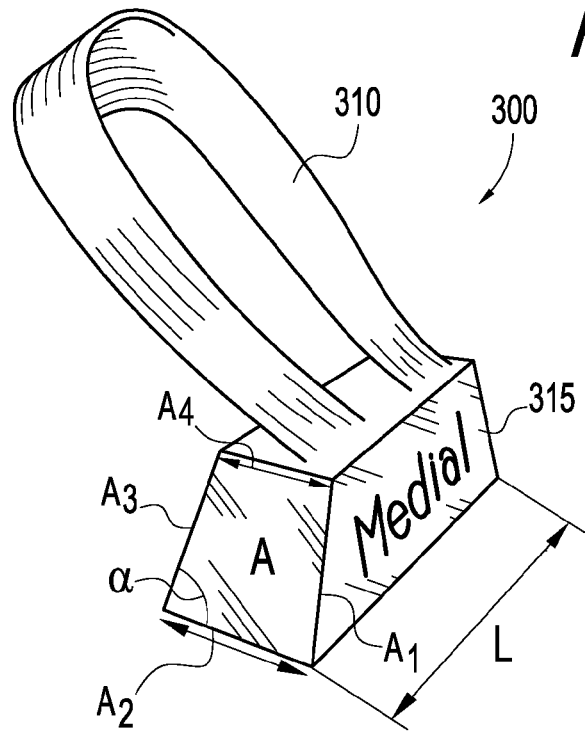
FIG. 8 illustrates a dovetail meniscal allograft implant.

A dovetail meniscus implant can be machined from allograft cortical bone using known techniques and is preferably a single piece of harvested material with the meniscus on a bone block. An exemplary dovetail meniscus implant 300 has a meniscus 310 hanging freely from bone block 315 as shown in FIG. 8. The dovetail configuration A is a cross-sectional trapezoidal shape with four edges A1 (height), A2 (base), A3 and A4 (small base), edges A1 and A2 forming a 90° angle and edges A2 and A3 forming an acute dovetail angle α, as shown in FIG. 8. Alternatively, the implant can be formed of a synthetic material, preferably a synthetic cortical bone material. A preferred synthetic material is tricalcium phosphate (TCP) and/or hyroxyapatite (HA), or a biodegradable polymer, preferably a polyactide, such as PLLA or a combination of some or all of the aforementioned materials.

Figure 2:
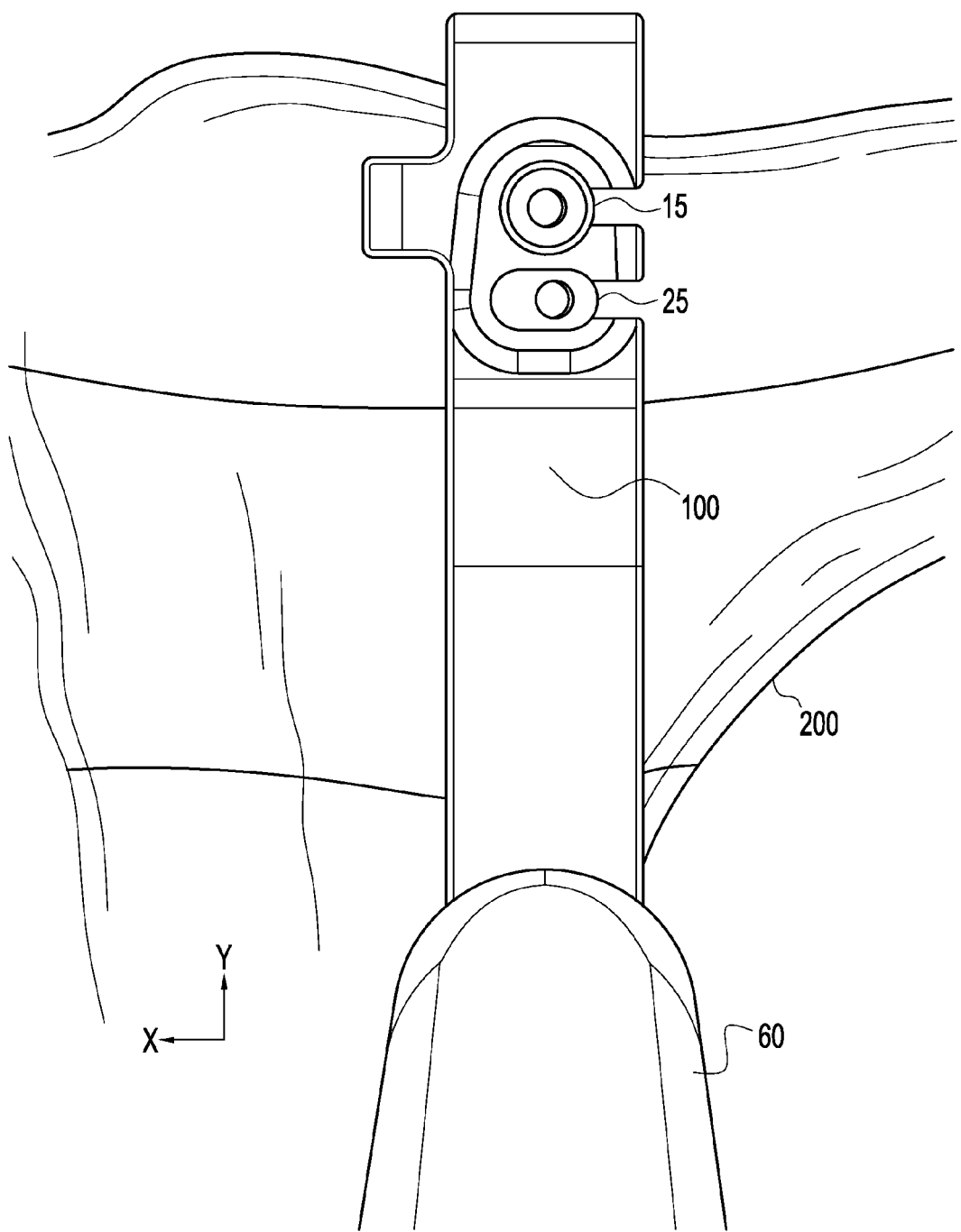
FIG. 2 illustrates an end view of the drill guide of FIG. 1, with the two drill sleeves in place.
Figure 3:
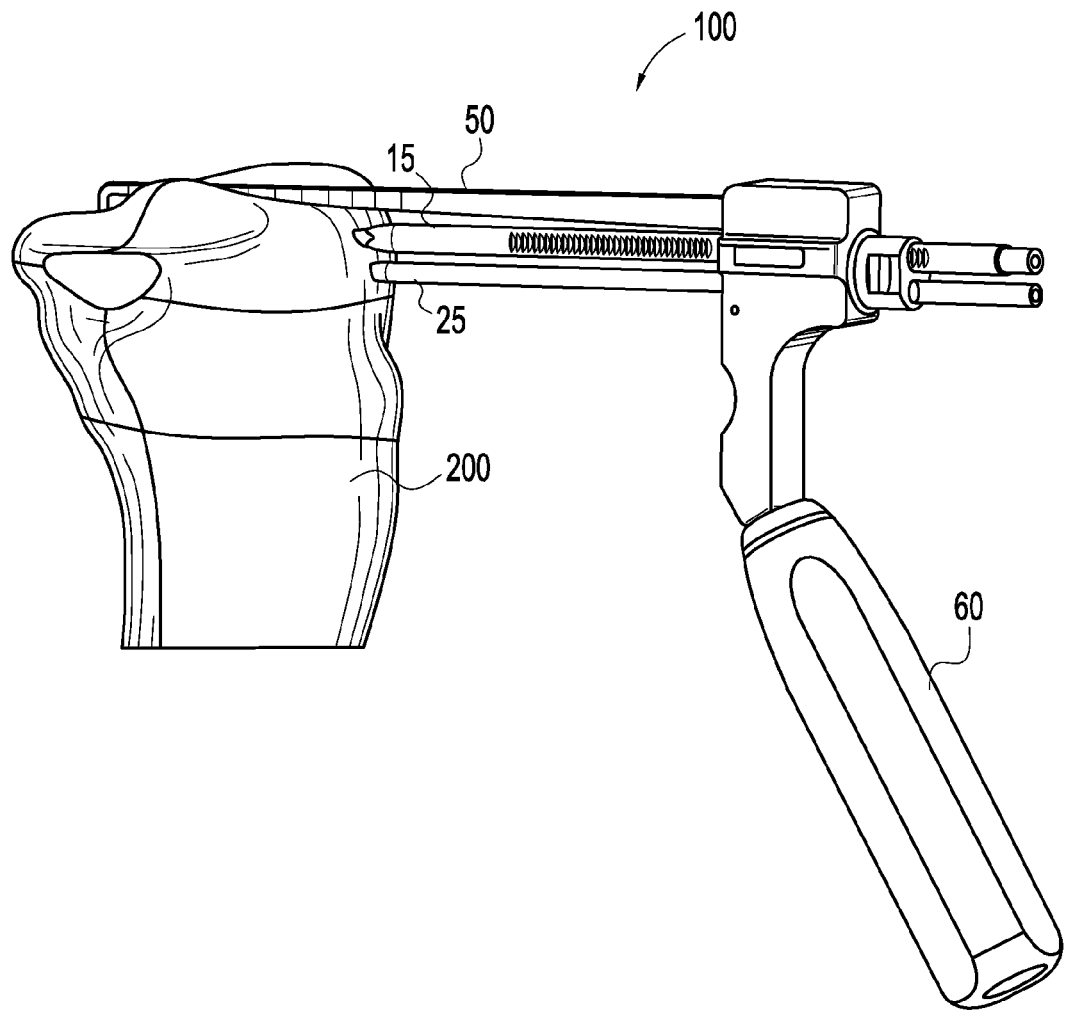
FIG. 3 illustrates a side view of the drill guide of FIG. 2.
Figure 4:
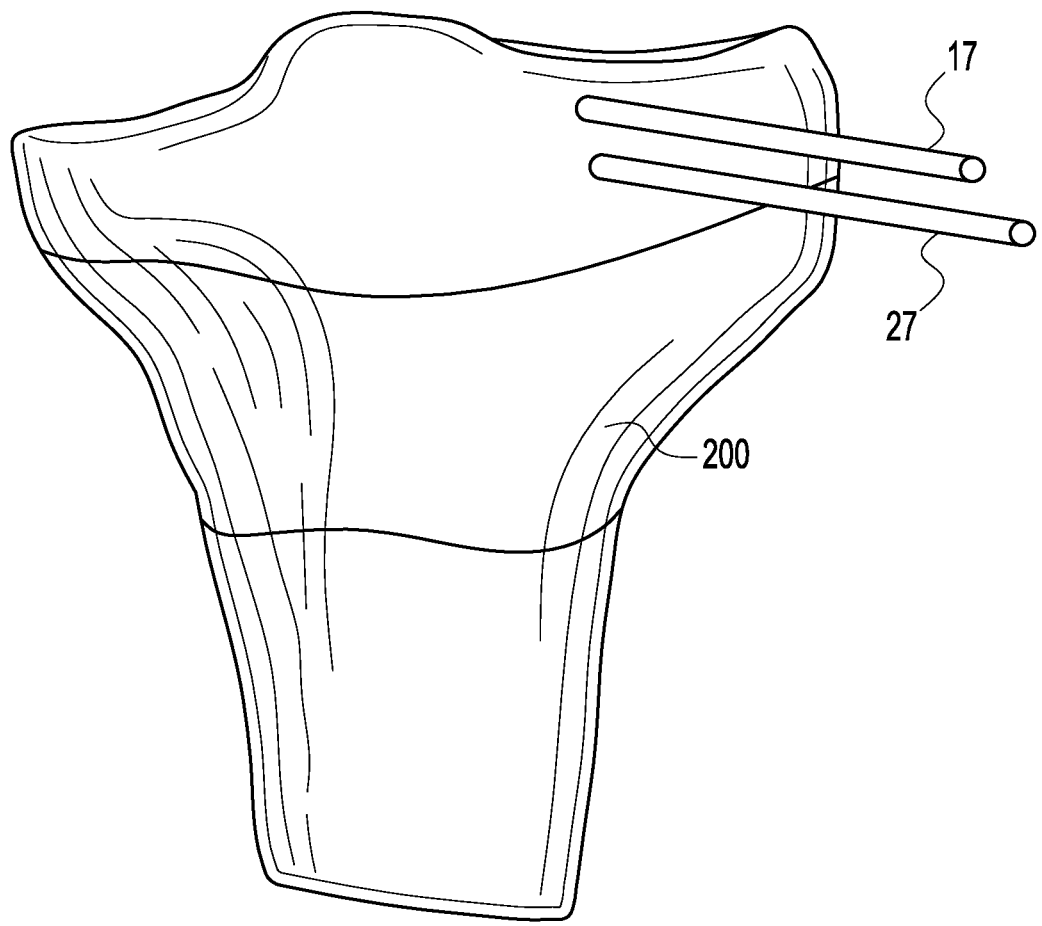
FIG. 4 illustrates the two guide pins left in place in the tibia after removal of the drill guide instrument.

Drill guide 100 of the present invention is illustrated in FIGS. 1-4. As shown in the drawings, drill guide 100 includes a marking hook 50 and handle 60. The drill guide 100 has a first opening 10 having a circular shape and a second opening 20 having an oblong or rectangular shape (FIG. 1). As shown in FIG. 2; first opening 10 is designed to receive drill sleeve 15. Drill sleeve 15 is cannulated to receive a guide pin 17 (FIG. 4). Second opening 20 is designed to receive a second drill sleeve 25 also cannulated to receive a guide pin 27 (FIG. 4). Second drill sleeve 25 may have an oblong or rectangular cross-section to allow for the cannulation to be offset from center as shown in FIG. 2. The oblong cross-section of the second drill sleeve 25 allows the second guide pin 27 to be placed either to the left or right of the center of guide pin 17 by simply flipping the drill sleeve 25 in opening 20.

An exemplary technique for forming a longitudinal groove having a dovetail cross-section in the tibia is described below. Drill guide 100 is placed proximate to the tibia 200 using the marking hook 50 to stabilize the drill guide in the desired position. FIG. 1 illustrates drill guide 100 positioned for drilling using marking hook 50. Drill sleeve 15 is placed through opening 10. Drill sleeve 25 is placed through opening 20. The drill sleeves do not have to be placed in any order, either one may be inserted first. Guide pins 17, 27 are inserted through the drill sleeves.

Figure 5:
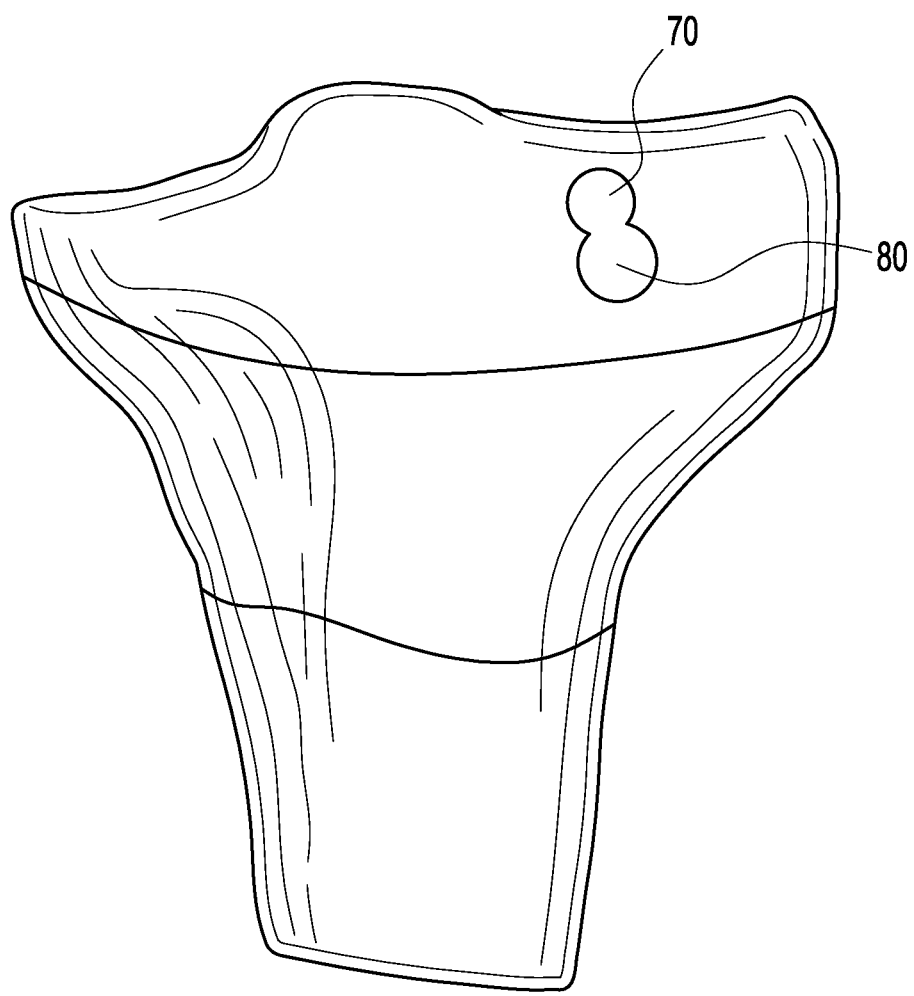
FIG. 5 illustrates a dovetail shape created in the tibia after reaming using the drill guide of FIG. 1.
Figure 6:
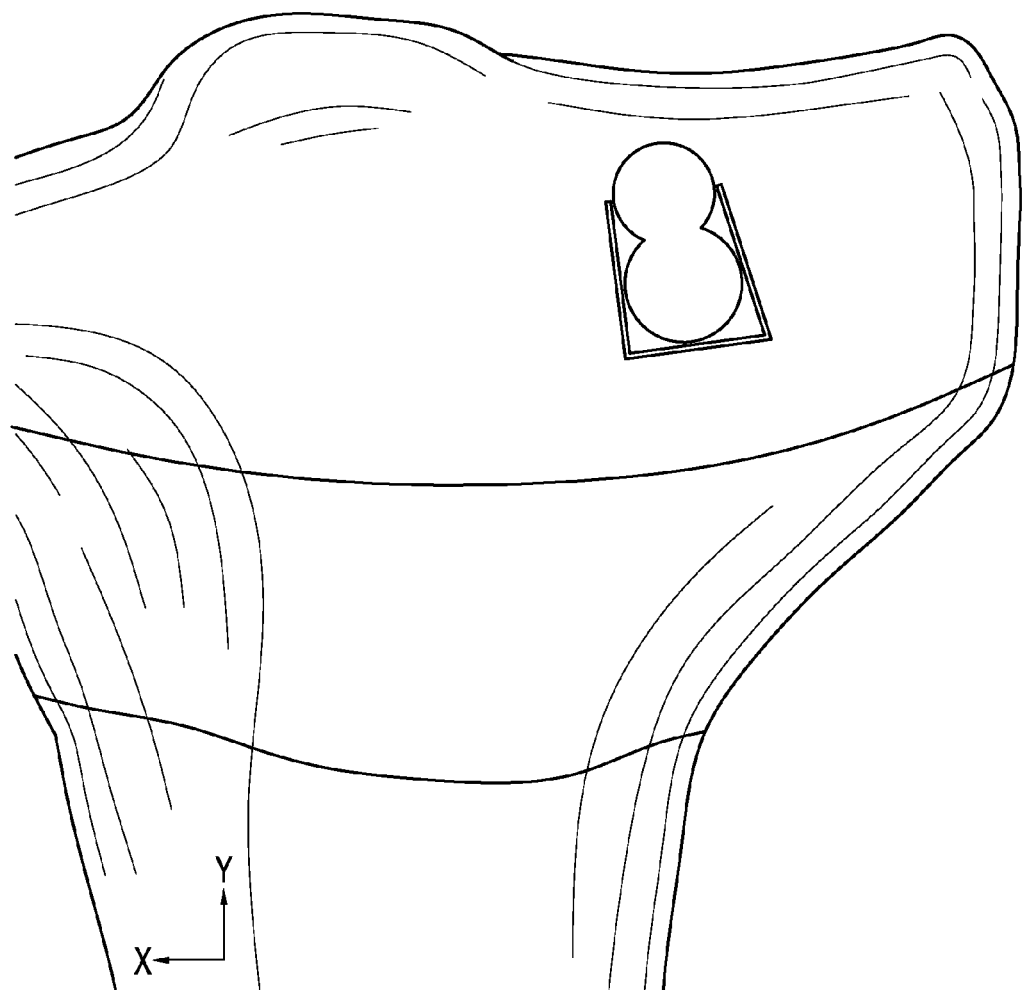
FIG. 6 illustrates the bone to be removed within the boxed area after the groove created with the drill guide of the present invention.
Figure 7:
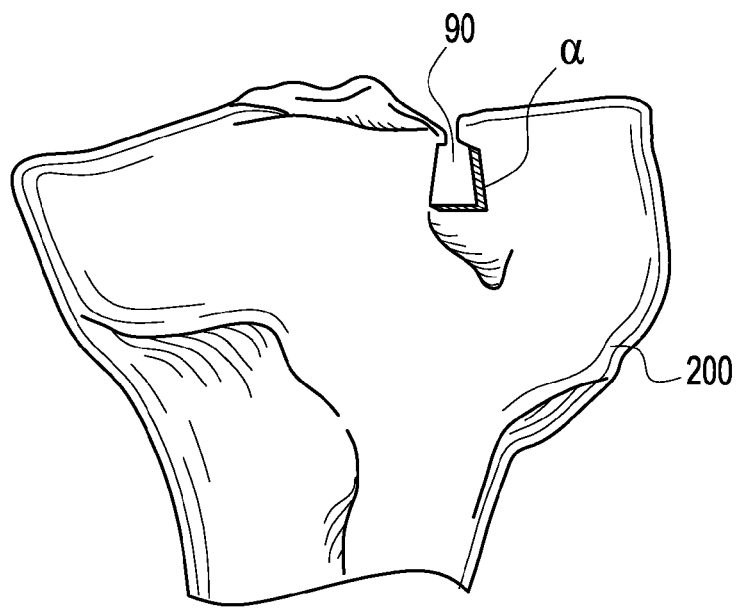
FIG. 7 illustrates the final groove created after removal of the bone in the boxed area shown in FIG. 6.

After placement of the guide pins, the entire drill guide instrument is removed leaving the guide pins 17, 27 in the bone as shown in FIG. 4. A reamer (not shown) is then used over guide pin 17 to create a first channel 70 in the bone. A second reamer (not shown) having a larger diameter than the first reamer is then used over guide pin 27 to create a second channel 80 overlapping or intersecting with the first channel 70, as shown in FIG. 5. The resulting groove is easier to then form into the desired dovetail cross-sectional groove to accommodate the dovetail meniscal allograft. A rasp or broach may be used to finalize the shape by removing the remaining bone shown in the outlined area in FIG. 6. The final dovetail shaped groove 90 is shown in FIG. 7.

Figure 9:
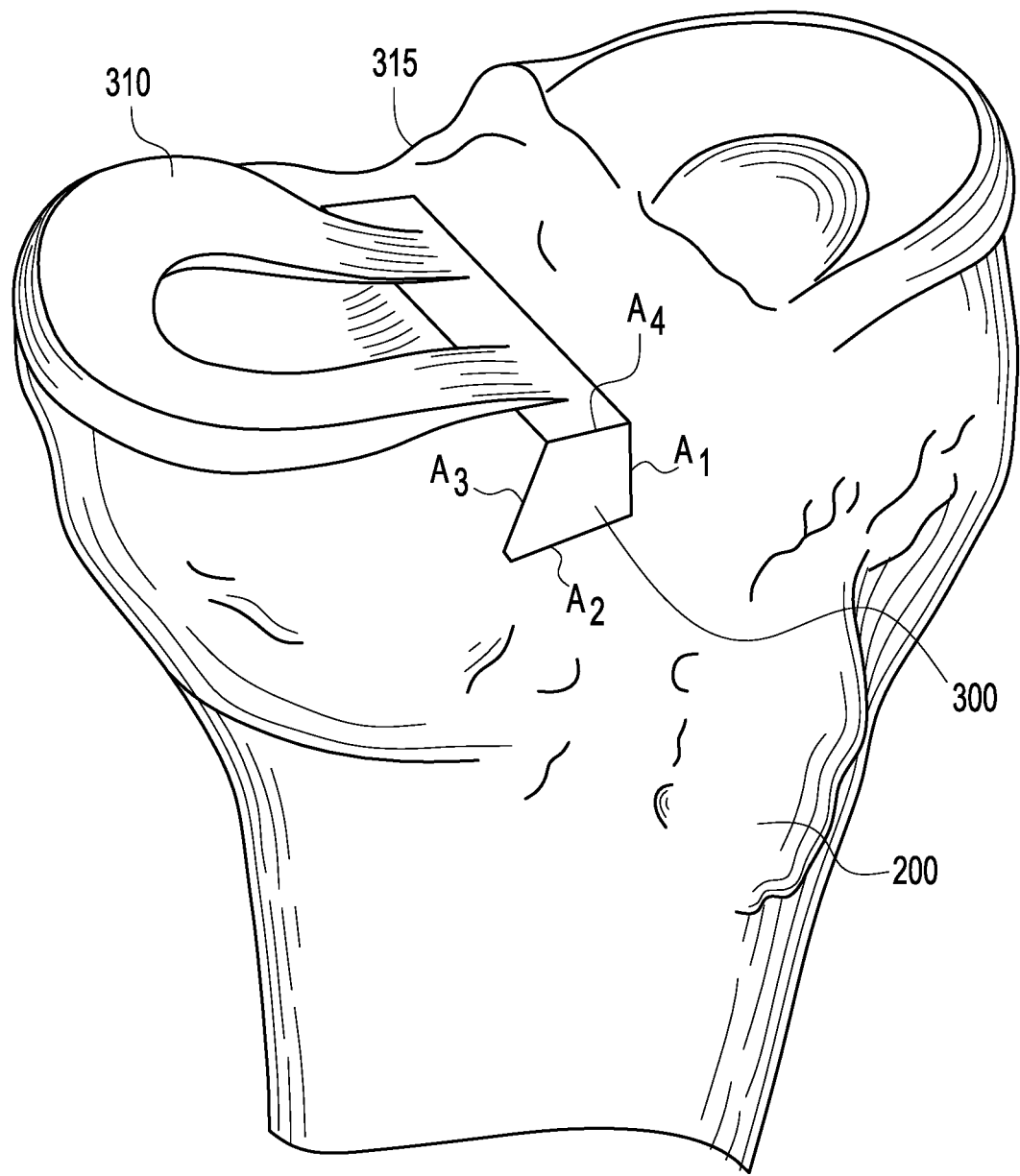
FIG. 9 illustrates the dovetail meniscal allograft implant of FIG. 8 inserted in the final groove of FIG. 7.

Finally, the dovetail meniscal allograft implant 300 (FIG. 8) is passed into the recipient dovetail tibial groove 90, as shown in FIG. 9. Any remaining bone debris in the dovetail groove is cleared. As the dovetail meniscal allograft implant is delivered to the tibial groove, the graft passing suture attached to the meniscal allograft implant is lead out the posterior lateral capsule via a standard inside out meniscal suturing technique. A meniscal allograft tamp may be employed to position the meniscal allograft implant into the dovetail tibial groove.

Figure 10:
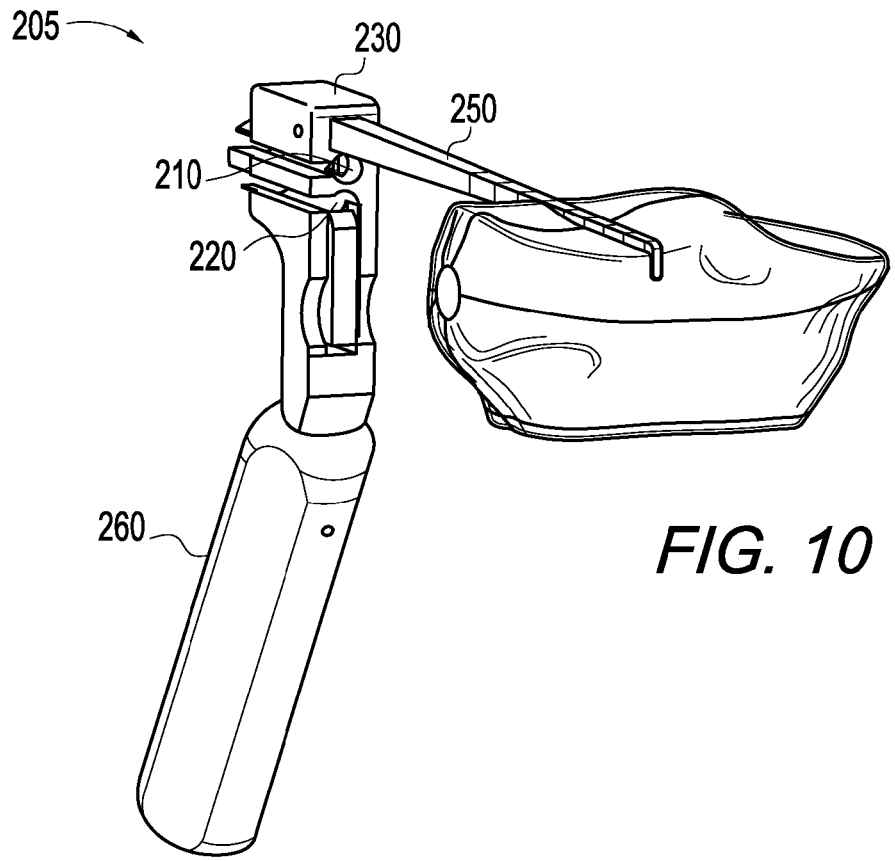
FIG. 10 illustrates a side view of another embodiment of a drill guide used for a meniscal allograft transplant procedure, with the marking hook positioning the drill guide with respect to the tibia.
Figure 11:
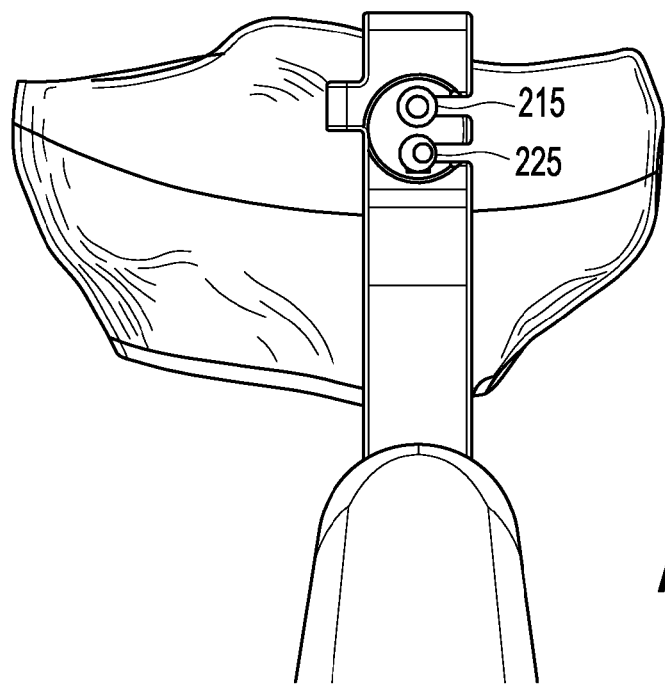
FIG. 11 illustrates an end view of the drill guide of FIG. 10, with the two drill sleeves in place.

Another embodiment is illustrated in FIGS. 10 and 11. In this embodiment, drill guide 205 includes a body 230, a marking hook 250, and a handle 260. The drill guide 205 has a first opening 210 having a circular shape and a second opening 220 having a circular shape. As shown in FIG. 11, first opening 210 is designed to receive drill sleeve 215. Drill sleeve 215 is cannulated to receive a guide pin. Second opening 220 is designed to receive a second drill sleeve 225 and is also cannulated to receive a guide pin. Second drill sleeve 225 is circular but the cannulated shaft is offset from center as shown in FIG. 11. The offset cannulated shaft of the second drill sleeve 225 allows the second guide pin to be placed either to the left or right of the center of guide pin by simply flipping the drill sleeve 225 in opening 220. Further, the cannulated shafts of the first and second drill sleeves 215, 225 have center points.

Although the present invention has been described in relation to particular embodiments thereof, many other variations and modifications and other uses will become apparent to those skilled in the art.

What is claimed as new and desired to be protected by Letters Patent of the United States is:

1. A method of allograft transplantation, the method comprising:
   providing a drill guide with a handle and a body, the body having first and second holes that extend through the body, the first hole being circular and the second hole being oblong, the first and second holes having respective centers;
   placing a first sleeve within the first hole, the first sleeve being circular and having a cannulation with a center which is aligned with the center of the first hole, such that the first sleeve is placed in a fixed location;
   placing a second sleeve within the second hole, the second sleeve having a cannulation with a center which is offset with respect to the center of the second hole, wherein a first line that intersects the centers of the first and second holes in a direction perpendicular to an axis of the body is non-parallel with a second line, co-planar with the first line, that intersects the centers of the cannulations of the first and second sleeves in the direction perpendicular to the axis of the body;
   placing a first guide pin within the cannulation of the first sleeve and into the bone and placing a second guide pin within the cannulation of the second sleeve and into the bone;
   subsequently, removing the drill guide leaving the first and second guide pins in the bone;
   using a first reamer having a first diameter over the first guide pin to create a first channel in the bone;
   using a second reamer, having a diameter larger than the first diameter, over the second guide pin to create a second channel in the bone, the second channel overlapping or intersecting the first channel and having a larger diameter than the first channel;
   forming a dovetail shaped groove in the bone shaped to accommodate a dovetail shaped allograft by removing bone from the edges of the overlapping first and second channels; and
   inserting the dovetail shaped allograft into the dovetail shaped groove.

2. The method of claim 1, wherein the bone is a tibia.

3. The method of claim 1, wherein the dovetail shaped allograft is a meniscal allograft.

4. The method of claim 1, further comprising using a marking hook to stabilize the body in the desired position.

* * * * *